(12) United States Patent
Li et al.

(10) Patent No.: US 8,308,713 B2
(45) Date of Patent: Nov. 13, 2012

(54) MEDICAL CATHETER ASSEMBLY INCLUDING MULTI-PIECE CONNECTOR

(75) Inventors: Changqing Li, Ellettsville, IN (US); Gary Wood, Spencer, IN (US); Herbert Alan Sundheimer, Ellettsville, IN (US); Laddvanh Bouphavichith, Worcester, MA (US); Patrice A. Weststrate, Norwood, MA (US); Laurence D. Brenner, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 368 days.

(21) Appl. No.: 12/383,354

(22) Filed: Mar. 23, 2009

(65) Prior Publication Data
US 2009/0182272 A1    Jul. 16, 2009

Related U.S. Application Data

(63) Continuation of application No. 10/440,009, filed on May 16, 2003, now Pat. No. 7,507,230, which is a continuation-in-part of application No. 10/078,223, filed on Feb. 19, 2002, now Pat. No. 6,802,836.

(51) Int. Cl.
*A61M 25/16* (2006.01)
*A61M 25/18* (2006.01)
*F16L 33/00* (2006.01)
*F16L 47/00* (2006.01)
*F16L 49/00* (2006.01)
*A61B 19/00* (2006.01)

(52) U.S. Cl. ......... 604/535; 604/408; 604/534; 285/242
(58) Field of Classification Search ............... 604/408, 604/534, 535; 285/242
See application file for complete search history.

(56) References Cited

U.S. PATENT DOCUMENTS
48,709 A * 7/1865 Emory .......................... 285/251
(Continued)

FOREIGN PATENT DOCUMENTS
DE       3314640 A1    11/1983
(Continued)

OTHER PUBLICATIONS
Japan Patent Office, Office Action in Japanese patent application No. 2003-569111, dated Apr. 2, 2009.
(Continued)

*Primary Examiner* — Nicholas Lucchesi
*Assistant Examiner* — Ian Holloway
(74) *Attorney, Agent, or Firm* — Kenyon & Kenyon LLP

(57) ABSTRACT

A medical catheter assembly including a multi-piece connector. In one embodiment, the medical catheter assembly is a PEG implanting assembly comprising a tubular dilator and a silicone feeding tube having an internal bolster at its rear end. The assembly also comprises a multi-piece connector comprising an inner ring, a fitting and an outer ring. The inner ring has an outer diameter greater than the inner diameter of the feeding tube and is coaxially disposed within the feeding tube by a friction-fit. The fitting comprises a front portion, an intermediate portion and a rear portion, the intermediate portion including a shoulder having an outer diameter greater than the inner diameter of the feeding tube. The front portion of the fitting is inserted through the rear end of the dilator and is secured to the dilator by a plurality of barbs. The shoulder and the rear portion of the fitting are inserted into the feeding tube through its rear end, with the rear portion of the fitting being inserted into the inner ring and secured thereto by mating threads. The outer ring is inserted over the feeding tube and is positioned between the shoulder and the inner ring, the outer ring being sized to securely retain the feeding tube between the outer ring and the inner ring and between the outer ring and the shoulder.

28 Claims, 12 Drawing Sheets

U.S. PATENT DOCUMENTS

| | | | |
|---|---|---|---|
| 362,297 A | 5/1887 | Albee et al. | |
| 1,217,203 A * | 2/1917 | Muehlberg | 285/247 |
| 2,782,058 A | 2/1957 | Clingman et al. | |
| 3,484,121 A * | 12/1969 | Quinton | 285/242 |
| 3,638,649 A | 2/1972 | Ersek | |
| 3,876,234 A | 4/1975 | Harms | |
| 3,926,187 A | 12/1975 | Iglesias | |
| 4,187,848 A | 2/1980 | Taylor | |
| 4,306,545 A | 12/1981 | Ivan et al. | |
| 4,390,017 A | 6/1983 | Harrison et al. | |
| 4,393,873 A | 7/1983 | Nawash et al. | |
| 4,417,890 A | 11/1983 | Dennehey et al. | |
| 4,424,833 A | 1/1984 | Spector et al. | |
| 4,473,369 A | 9/1984 | Lueders et al. | |
| 4,511,163 A | 4/1985 | Harris et al. | |
| 4,557,261 A | 12/1985 | Rugheimer | |
| 4,588,402 A * | 5/1986 | Igari et al. | 604/408 |
| 4,642,091 A | 2/1987 | Richmond | |
| 4,774,944 A | 10/1988 | Mischinski | |
| 4,826,477 A | 5/1989 | Adams | |
| 4,834,712 A | 5/1989 | Quinn et al. | |
| 4,861,334 A | 8/1989 | Nawaz | |
| 4,863,438 A | 9/1989 | Gauderer et al. | |
| 4,895,570 A * | 1/1990 | Larkin | 604/411 |
| 4,900,306 A | 2/1990 | Quinn et al. | |
| 4,944,732 A | 7/1990 | Russo | |
| 4,946,200 A * | 8/1990 | Blenkush et al. | 285/38 |
| 4,951,976 A | 8/1990 | Boelkins | |
| 5,007,900 A | 4/1991 | Picha et al. | |
| 5,024,655 A | 6/1991 | Freeman | |
| 5,026,352 A | 6/1991 | Anderson | |
| 5,071,405 A | 12/1991 | Piontek et al. | |
| 5,100,394 A | 3/1992 | Dudar et al. | |
| 5,112,310 A | 5/1992 | Grobe | |
| 5,158,569 A | 10/1992 | Strickland et al. | |
| 5,167,627 A | 12/1992 | Clegg et al. | |
| 5,176,415 A | 1/1993 | Choksi | |
| 5,178,423 A | 1/1993 | Combeau | |
| 5,215,538 A | 6/1993 | Larkin | |
| 5,222,772 A | 6/1993 | McGraw | |
| 5,259,399 A | 11/1993 | Brown | |
| 5,267,983 A | 12/1993 | Oilschlager et al. | |
| 5,290,250 A | 3/1994 | Bommarito | |
| 5,323,811 A * | 6/1994 | Hohmann et al. | 137/614.04 |
| 5,358,488 A | 10/1994 | Suriyapa | |
| 5,391,159 A * | 2/1995 | Hirsch et al. | 604/268 |
| 5,405,339 A * | 4/1995 | Kohnen et al. | 604/535 |
| 5,488,949 A | 2/1996 | Kreifels et al. | |
| 5,505,714 A * | 4/1996 | Dassa et al. | 604/534 |
| 5,549,657 A * | 8/1996 | Stern et al. | 604/537 |
| 5,720,734 A | 2/1998 | Copenhaver et al. | |
| 5,782,508 A * | 7/1998 | Bartholomew | 285/319 |
| 5,830,195 A | 11/1998 | Peters et al. | |
| 5,836,924 A | 11/1998 | Kelliher et al. | |
| 5,863,366 A | 1/1999 | Snow | |
| 6,050,987 A | 4/2000 | Rosenbaum | |
| 6,095,997 A | 8/2000 | French et al. | |
| 6,802,836 B2 | 10/2004 | Bouphavichith et al. | |
| 6,971,390 B1 | 12/2005 | Vasek et al. | |
| 7,641,648 B2 * | 1/2010 | Bouphavichith et al. | 604/533 |

FOREIGN PATENT DOCUMENTS

| | | |
|---|---|---|
| EP | 0976418 A1 | 2/2000 |
| GB | 2055166 A | 2/1981 |
| JP | 49148423 A1 | 12/1974 |
| JP | 62281962 A | 12/1987 |
| JP | 3280971 A | 12/1991 |
| JP | 33-18463 A | 10/1996 |
| JP | 9508542 A | 9/1997 |
| JP | 9508840 T | 9/1997 |
| JP | 11-141791 A | 5/1999 |
| JP | 2000506051 T | 5/2000 |
| WO | 95/20936 A1 | 8/1995 |
| WO | 95/22369 A1 | 8/1995 |
| WO | 9732623 A1 | 9/1997 |

OTHER PUBLICATIONS

Japan Patent Office, Office Action in Japanese patent application No. 2006-533180, dated Aug. 31, 2010.

European Patent Office, partial International Search Report in International Application No. PCT/EP03/01443, mailed Nov. 10, 2001.

Printout of www.barblock.com on Mar. 27, 2003.

European Patent Office, International Search Report from PCT/US2004/015541, the corresponding PCT application to U.S. Appl. No. 10/440,009, dated Nov. 19, 2004.

Australian Patent Office, Examiner's First Report on related patent application No. 2003205762, dated Jul. 27, 2007.

Japan Patent Office, Office Action in related Japanese Patent Application No. 2003-56911 dated Jan. 5, 2010.

Japan Patent Office, Office Action in related Japanese Patent Application No. 2006-533180, dated Nov. 24, 2009.

* cited by examiner

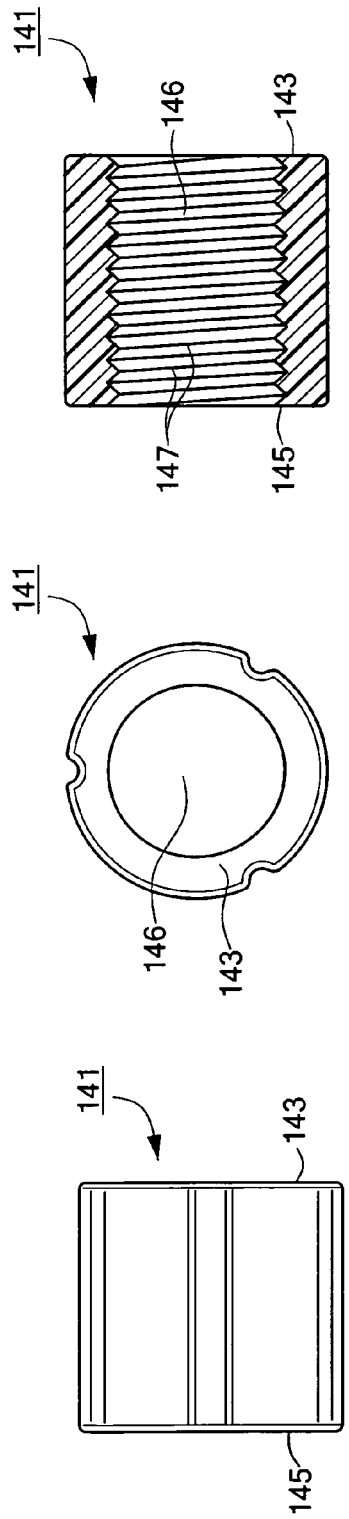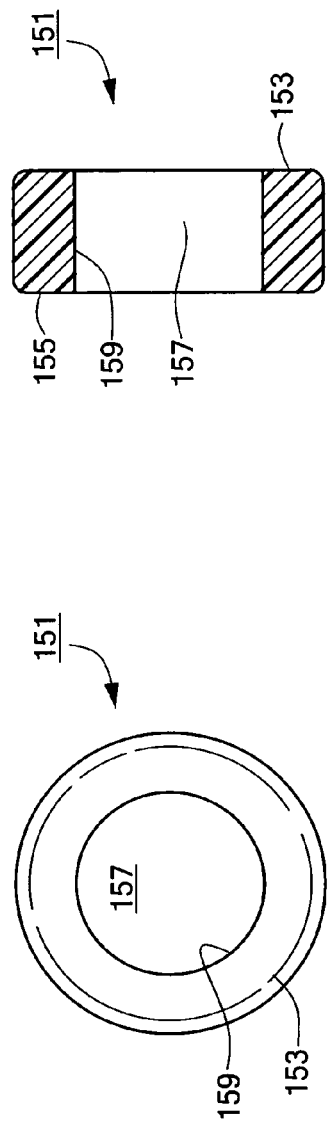

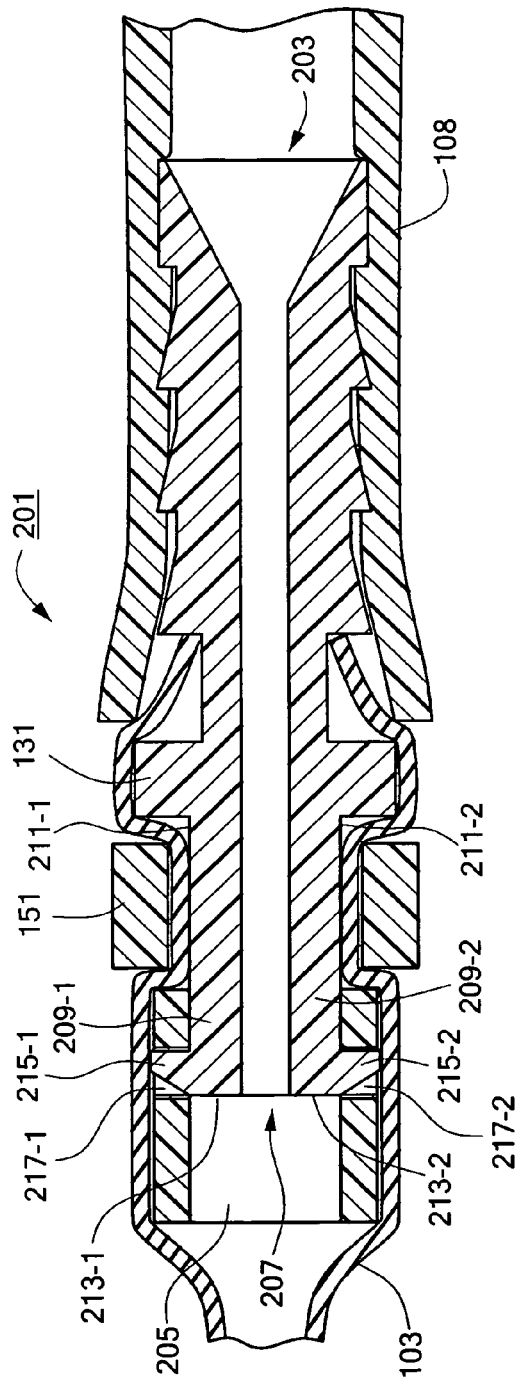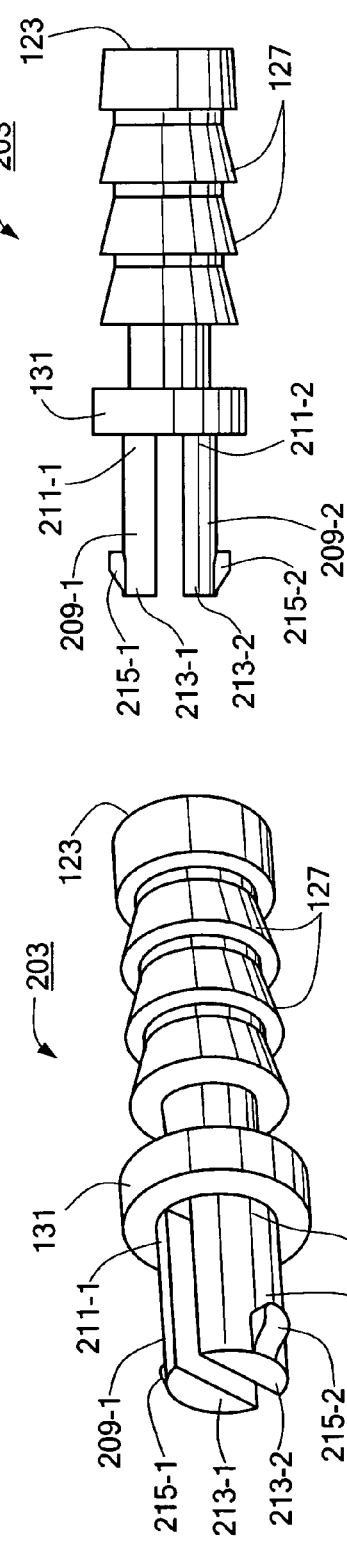
FIG. 9
FIG. 10(a)
FIG. 10(b)

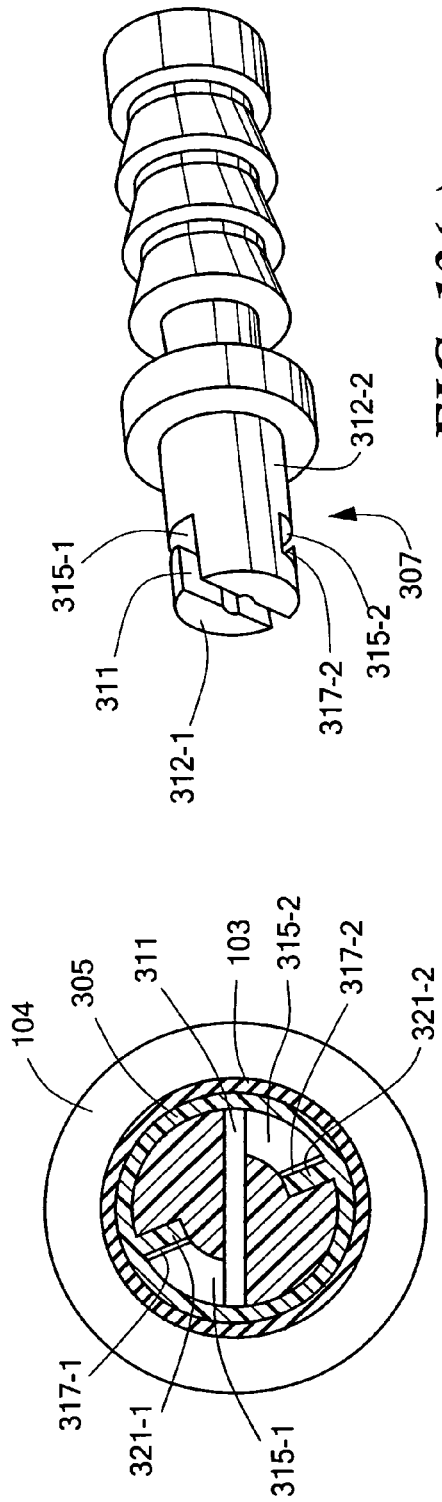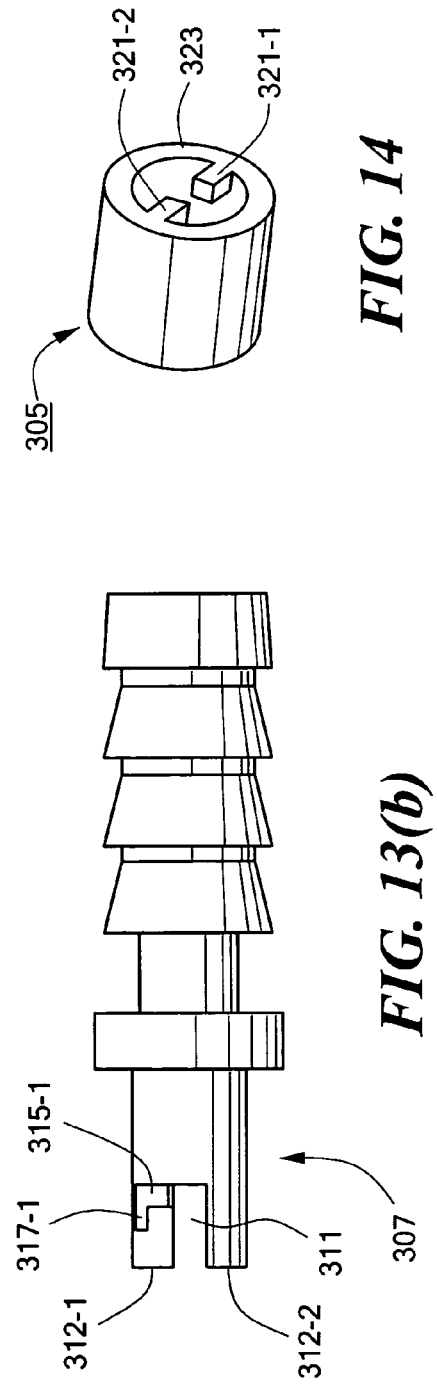

MEDICAL CATHETER ASSEMBLY INCLUDING MULTI-PIECE CONNECTOR

CROSS-REFERENCE TO RELATED APPLICATIONS

The present application is a continuation of U.S. patent application Ser. No. 10/440,009, filed May 16, 2003, now U.S. Pat. No. 7,507,230, which in turn is a continuation-in-part of U.S. patent application Ser. No. 10/078,223, filed Feb. 19, 2002, now U.S. Pat. No. 6,802,836, both of which are incorporated herein by reference.

BACKGROUND OF THE INVENTION

The present invention relates generally to medical catheters, such as gastrostomy feeding tubes, and relates more particularly to medical catheter assemblies, such as percutaneous endoscopic gastrostomy (PEG) implanting assemblies.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a catheter/bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the gastric wall.

With the internal bolster in place against the gastric wall, a proximal portion of the implanted gastrostomy feeding tube is then typically cut and removed from the implanted tube to reduce the externally-extending portion of the tube to a desired length. (The removal of the proximal portion of the gastrostomy feeding tube also results in the removal of the dilator, which is connected thereto.) An external bolster is typically secured to the remaining implanted portion of the feeding tube to engage the abdomen in such a way as to prevent longitudinal movement of the feeding tube within the stoma tract. Additionally, a "Y-port" adapter is typically attached to the proximal end of the implanted feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

As can readily be appreciated, because the leading end of the gastrostomy feeding tube is drawn through the abdomen by pulling on the dilator, the connection between the dilator and the gastrostomy feeding tube must be strong enough to withstand the tensile force applied thereto. Otherwise, the gastrostomy feeding tube may separate from the dilator prior to emergence of the feeding tube from the patient, thereby requiring the feeding tube to be retrieved from the patient and possibly leading to undesired complications. For connections like the aforementioned connection between the gastrostomy feeding tube and the dilator of a push-type catheter implanting assembly, the industry standard minimum tensile strength is 17 pounds (see BS EN 1615:2000).

Historically, however, this standard has not typically been met by the conventional type of connection used to couple a dilator to a gastrostomy feeding tube. An example of such a connection typically comprises an appropriately dimensioned tubular fitting having barbs at opposite ends thereof. One end of the tubular fitting is inserted into the trailing end of the dilator, and the opposite end of the fitting is inserted into the leading end of the gastrostomy feeding tube. The connection also comprises a short length of plastic tubing, which is shrink-wrapped around the trailing end of the dilator and the leading end of the feeding tube (as well as surrounding the fitting disposed within the trailing end of the dilator and the leading end of the feeding tube).

In addition to failing frequently to meet the minimum tensile strength required for a connection between a dilator and a feeding tube, other shortcomings with the above-described connection are (i) that the application of the shrink-wrapped length of tubing to the assembly requires the expenditure of time and labor, (ii) that the shrink-wrapped tubing undesirably increases the cross-sectional profile of the assembly, and (iii) that there is a widespread perception that the ends of the shrink-wrapped tubing, which ends do not lie flush with the dilator or the feeding tube, may snag tissue as the assembly makes its winding path through the patient.

According to the pull method, the distal end of an endoscope is inserted into a patient's mouth and is passed through the esophagus into the stomach. After distension of the stomach by inflation, an entry site on the abdomen is identified, and an incision is made by passing a needle with an outer cannula (e.g., a Seldinger needle) through the abdominal wall and into the stomach. The needle is then removed while keeping the cannula in place. Next, a snare is inserted into the stomach via the endoscope and is looped over the distal end of the cannula. A first end of a suture is then passed through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly comprising a gastrostomy feeding tube having an internal bolster at its trailing end and a plastic fitting at its leading end. The plastic fitting has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop.

Using the second end of the suture, the pull-type catheter implanting assembly is then pulled retrograde through the patient until the gastrostomy feeding tube emerges from the abdomen of the patient and the internal bolster engages the gastric wall of the patient. Next, as is the case in the push method, the implanted gastrostomy feeding tube is typically cut to a desired length, an external bolster is typically secured to the cut implanted tube, a "Y-port" adapter is typically attached to the proximal end of the implanted feeding tube, and a detachable locking clip is typically secured to the implanted feeding tube at a point between the external bolster and the Y-port adapter.

As can readily be appreciated, because the pull-type catheter assembly is moved into position within the patient's body by pulling on the suture, it is very important that the plastic fitting maintain its coupling to the gastrostomy feeding tube.

SUMMARY OF THE INVENTION

It is an object of the present invention to provide a novel medical catheter assembly.

It is another object of the present invention to provide a medical catheter assembly as described above that overcomes at least some of the problems described above in connection with existing medical catheter assemblies of the type used to implant PEG devices.

The present invention is based, at least in part, on the present inventors' recognition that certain existing PEG-implanting assemblies fail to withstand the considerable separation force that is applied during implantation. This failure is largely attributable to the fact that a strong connection cannot be maintained between a gastrostomy feeding tube, which is typically made of silicone rubber, and a (push-type or pull-type) dilator, which is typically not made of silicone rubber, but rather, is typically made of a thermoplastic material.

Therefore, according to one aspect of the invention, there is provided a medical catheter assembly, said medical catheter assembly comprising (a) a medical catheter, said medical catheter being made of an elastic material and having a front end, a rear end and an inner diameter; (b) a first tubular member, said first tubular member having an outer diameter greater than the inner diameter of said medical catheter, said first tubular member being coaxially disposed within said medical catheter and secured thereto by a friction-fit; (c) a fitting, said fitting comprising a shoulder and a rear portion, said shoulder being positioned in front of said rear portion and having an outer diameter greater than the inner diameter of said medical catheter, said shoulder and said rear portion being inserted into said medical catheter through said front end, with said rear portion inserted into said first tubular member and secured thereto; and (d) a second tubular member, said second tubular member being inserted over said medical catheter and positioned between said shoulder and said first tubular member, said second tubular member being appropriately sized to securely retain said medical catheter between said second tubular member and said first tubular member and to securely retain said medical catheter between said second tubular member and said shoulder.

In one embodiment, the aforementioned medical catheter assembly is a pull-type PEG implanting assembly. In such an embodiment, the fitting preferably further comprises a front portion in front of said shoulder, said front portion extending beyond said front end of said medical catheter, said front portion being conical in shape and coming to a tip at a front end of said fitting. A wire loop is preferably secured to said fitting, for example by insert-molding, and extends forwardly from the front end of said fitting.

In another embodiment, the above-described medical catheter assembly is a push-type PEG implanting assembly. In such an embodiment, the assembly preferably further comprises a tubular dilator, and the fitting preferably further comprises a front portion in front of said shoulder, said front portion extending beyond said front end of said medical catheter and being secured within the rear end of the tubular dilator, for example by barbs formed on said fitting engageable with the inner surface of said dilator. The fitting is preferably further provided with a longitudinal bore through which a guidewire may be passed.

In both the pull-type and push-type PEG implanting assemblies described above, the rear portion of the fitting may be secured to the first tubular member in a variety of different ways. For example, the fitting rear portion and the first tubular member may be joined together by the mating engagement of threads, one such thread being provided on the interior surface of the first tubular member and the other thread being provided on the exterior surface of the fitting rear portion. Alternatively, the fitting rear portion may be shaped to include a pair of resilient legs having outwardly-facing, opposing feet, and the first tubular member may be shaped to include transverse openings adapted to receive the outwardly-facing, opposing feet. Alternatively, the fitting rear portion and the first tubular member may be joined together by spin-welding. Alternatively, the fitting rear portion and the first tubular member may be complementarily shaped to permit being joined in a push-twist-pull fashion.

The present invention is also directed to a medical catheter assembly, said medical catheter assembly comprising (a) a medical catheter; (b) a first tubular member, said first tubular member being secured within said medical catheter; and (c) a fitting, said fitting comprising a rear portion, said rear portion being positioned within said first tubular member and secured thereto.

The present invention is additionally directed to a connector for connecting a first length of tubing to a second length of tubing, the first length of tubing being made of an elastic material, said connector comprising (a) a first tubular member, said first tubular member having an outer diameter greater than the inner diameter of said first length of tubing, said first tubular member being adapted to be coaxially inserted into said first length of tubing and secured therewithin by a friction-fit; (b) a fitting, said fitting comprising a front portion, a shoulder and a rear portion, said shoulder being positioned between said front portion and said rear portion and having an outer diameter greater than the inner diameter of said first length of tubing, said shoulder and said rear portion being adapted to be coaxially inserted into said first length of tubing, said rear portion of said fitting being adapted to be coaxially inserted into said first tubular member and secured thereto, said front portion of said fitting being adapted to be coaxially inserted into said second length of tubing and secured thereto; and (c) a second tubular member, said second tubular member being adapted to be inserted over said first length of tubing and positioned between said shoulder and said first tubular member, said second tubular member being appropriately sized so that, with said fitting and said first tubular member secured to one another, said first length of tubing may be securely retained between said second tubular member and said first tubular member and between said second tubular member and said shoulder.

The present invention is further directed to a connector for use with a first length of tubing, the first length of tubing being made of an elastic material, said connector comprising (a) a first tubular member, said first tubular member having an outer diameter greater than the inner diameter of said first length of tubing, said first tubular member being adapted to be coaxially inserted into said first length of tubing and secured therewithin by a friction-fit; (b) a fitting, said fitting comprising a front portion, a shoulder and a rear portion, said shoulder being positioned between said front portion and said rear portion and having an outer diameter greater than the inner diameter of said first length of tubing, said shoulder and said rear portion being adapted to be coaxially inserted into said first length of tubing, with said rear portion of said fitting being adapted to be coaxially inserted into said first tubular member and secured thereto, said front portion of said fitting being conical in shape and terminating in a tip at a front end thereof; (c) a wire loop extending forwardly from said front end of said fitting; and (d) a second tubular member, said second tubular member being adapted to be inserted over said first length of tubing and positioned between said shoulder and said first tubular member, said second tubular member being appropriately sized so that, with said fitting and said first tubular member secured to one another, said first length of tubing may be securely retained between said second tubular member and said first tubular member and between said second tubular member and said shoulder.

For purposes of the present specification and claims, various relational terms like "top," "bottom," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown, by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 7(a) through 7(c) are enlarged side, end, and section views, respectively, of the inner ring member shown in FIG. 4;

FIGS. 8(a) and 8(b) are enlarged end and section views, respectively, of the outer ring member shown in FIG. 4;

FIG. 9 is a fragmentary, longitudinal section view of a second embodiment of a medical catheter assembly constructed according to teachings of the present invention, said medical catheter assembly being adapted for percutaneous endoscopic use in a patient using the push method;

FIGS. 10(a) and 10(b) are perspective and side views, respectively, of the fitting shown in FIG. 9;

FIG. 12(b) is a transverse section view of the medical catheter assembly of FIG. 12(a), illustrating the locking together of the fitting and the inner ring;

FIGS. 13(a) and 13(b) are perspective and side views, respectively, of the fitting shown in FIG. 12(a);

FIG. 14 is a perspective view of the inner ring shown in FIG. 12(a);

DETAILED DESCRIPTION OF PREFERRED EMBODIMENTS

Figure 1:
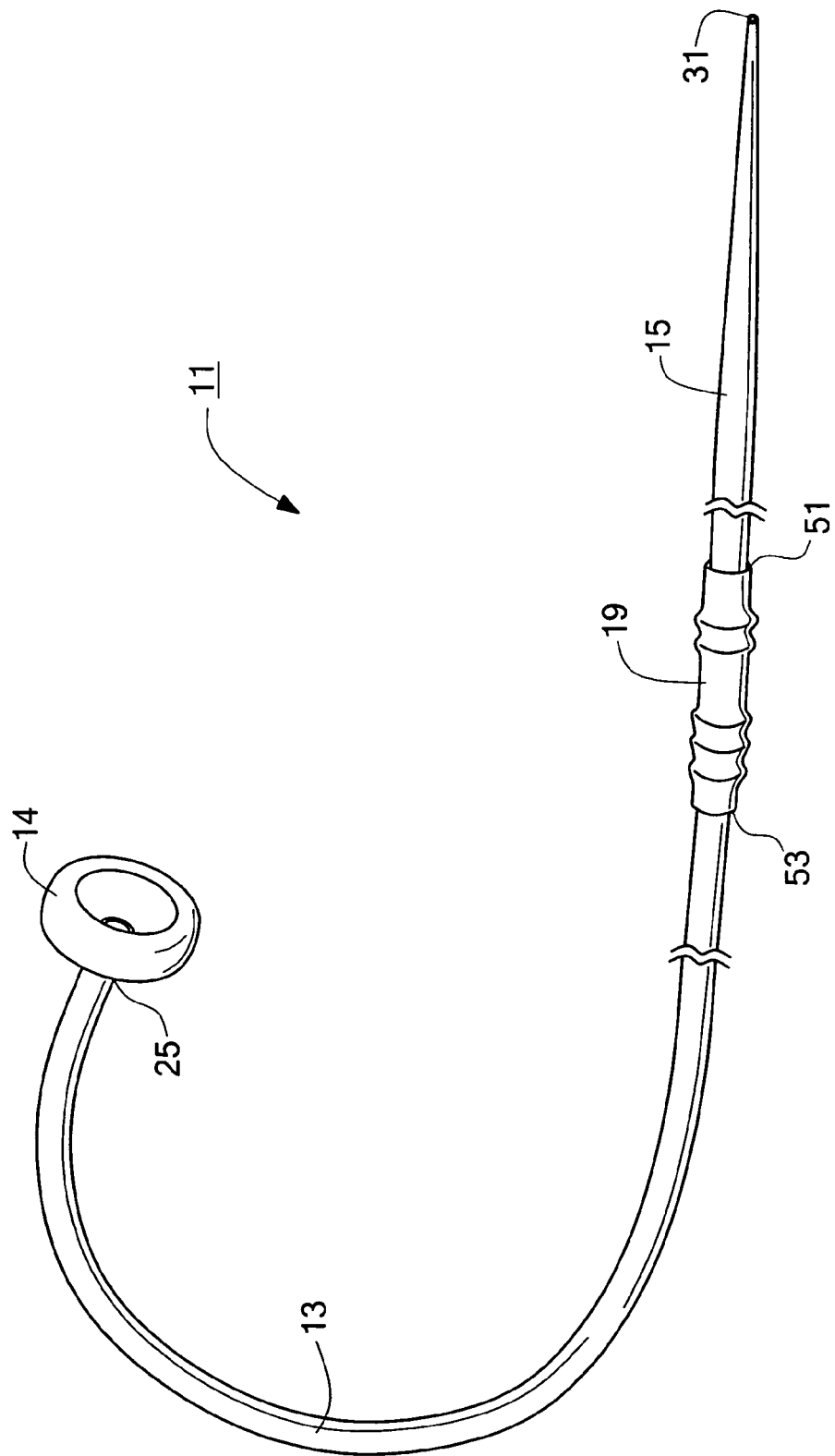
FIG. 1 is a fragmentary, perspective view of a conventional medical catheter assembly adapted for percutaneous endoscopic implantation in a patient using the push method.
Figure 2:
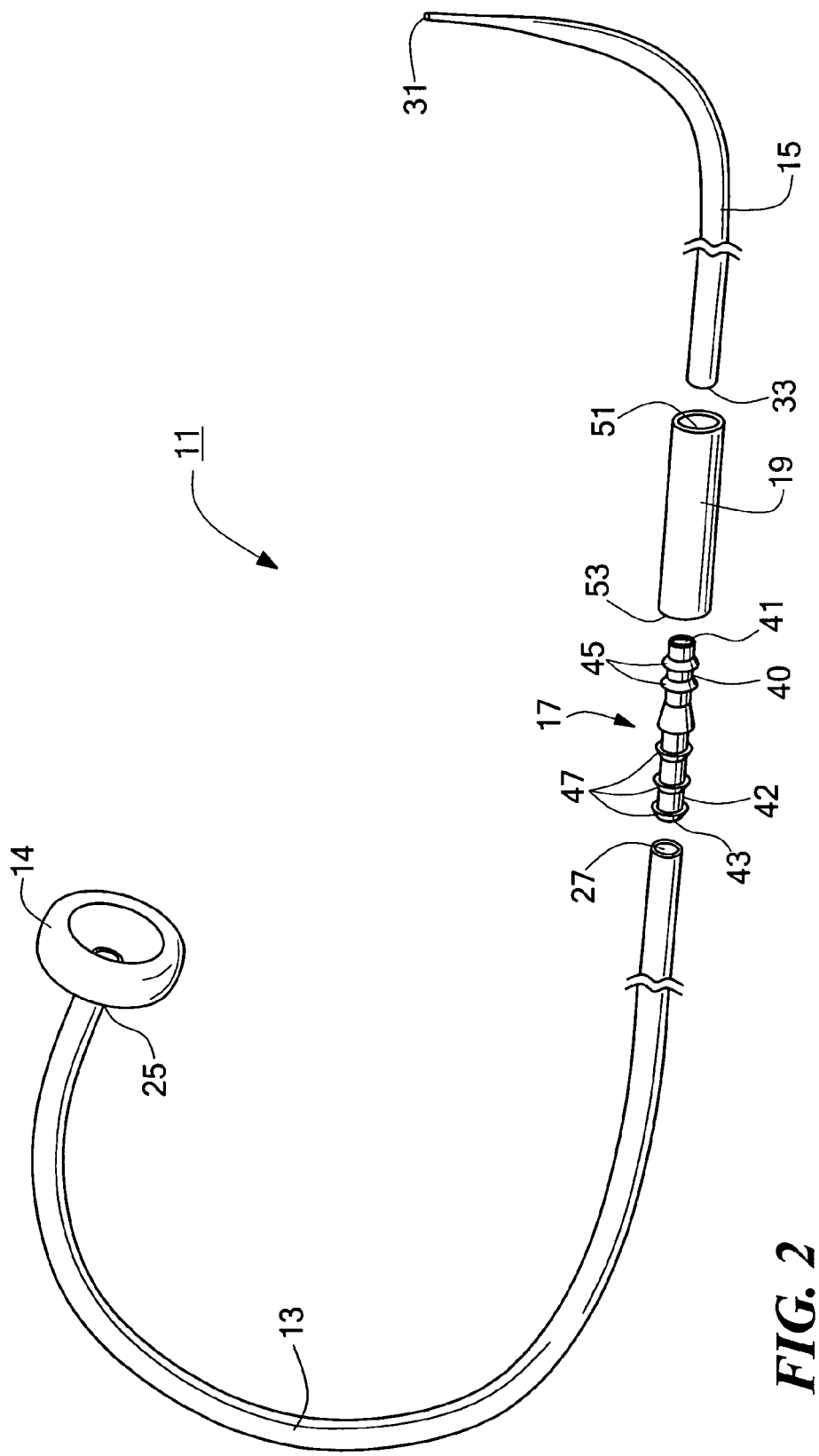
FIG. 2 is a fragmentary, exploded, perspective view of the conventional medical catheter assembly of FIG. 1 prior to the heat-shrinking of the short plastic tubing.

Referring now to FIGS. 1 and 2, there are shown fragmentary, perspective and fragmentary, exploded, perspective views, respectively, of a conventional medical catheter assembly adapted for percutaneous endoscopic implantation in a patient using the push method, said conventional medical catheter assembly being represented generally by reference numeral 11.

Assembly 11, which is shown prior to use on a patient, comprises a gastrostomy feeding tube 13, an internal bolster 14, a dilator 15, a fitting 17 and a short length of tubing 19.

Tube 13, which is made of a soft, biocompatible, silicone rubber, is an elongated, tubular member having a trailing end 25 and a leading end 27. A series of ruler markings (not shown) are printed on tube 13 and extend several inches from trailing end 25 in the direction of leading end 27 to facilitate the cutting of tube 13 to a desired length after it has been implanted in a patient.

Internal bolster 14, which is also made of a soft, biocompatible, silicone rubber, is securely disposed at trailing end 25 of tube 13 and, in the present embodiment, forms a unitary structure therewith.

Dilator 15, which is made of a polyethylene having sufficient rigidity to open a stoma and sufficient flexibility to permit its being bent through a patient, is a tubular member having a leading end 31 and a trailing end 33. Dilator 15 is dimensioned to gradually increase in diameter over a length of several inches from leading end 31, which is sized to conform closely to a guidewire inserted thereinto, to trailing end 33, which is sized to approximate the dimensions of leading end 27 of tube 13.

Fitting 17, which is made of a rigid plastic, is a unitary tubular member having a front portion 40 and a rear portion 42, front portion 40 beginning with a leading end 41, rear portion 42 terminating in a trailing end 43. Front portion 40 is inserted into dilator 15 through trailing end 33 and is secured within dilator 15 by a series of external barbs 45 extending rearwardly from leading end 41. Rear portion 42 is inserted into gastrostomy feeding tube 13 through leading end 27 and is secured within tube 13 by a series of external barbs 47 extending forwardly from trailing end 43.

Tubing 19, which is a unitary member made of a heat-shrinkable material, is shaped to include a leading end 51 inserted over trailing end 33 of dilator 15 (as well as over leading end 41 of fitting 17) and a trailing end 53 inserted over leading end 27 of tube 13 (as well as over trailing end 43 of fitting 17). As can be seen in FIG. 1, because tubing 19 is tightly fitted over tube 13, dilator 15, and fitting 17, tubing 19 helps to soften the transition of outer dimensions among the various components.

However, as noted above, despite the reinforcement to the connection provided by tubing 19, assembly 11 often fails to withstand tensile forces in the range of about 17 pounds and, therefore, does not meet industry standards, such as BS EN 1615:2000. In addition, the application of tubing 19 to its underlying components adds time and labor and, therefore, expense to the manufacture of assembly 11. Furthermore, tubing 19 adds to the cross-sectional profile of assembly 11, and there is a widespread perception in the industry that ends 51 and 53 of tubing 19, which do not lie flush with dilator 15 or feeding tube 13, may snag tissue as assembly 11 winds its way through a patient.

Figure 3:
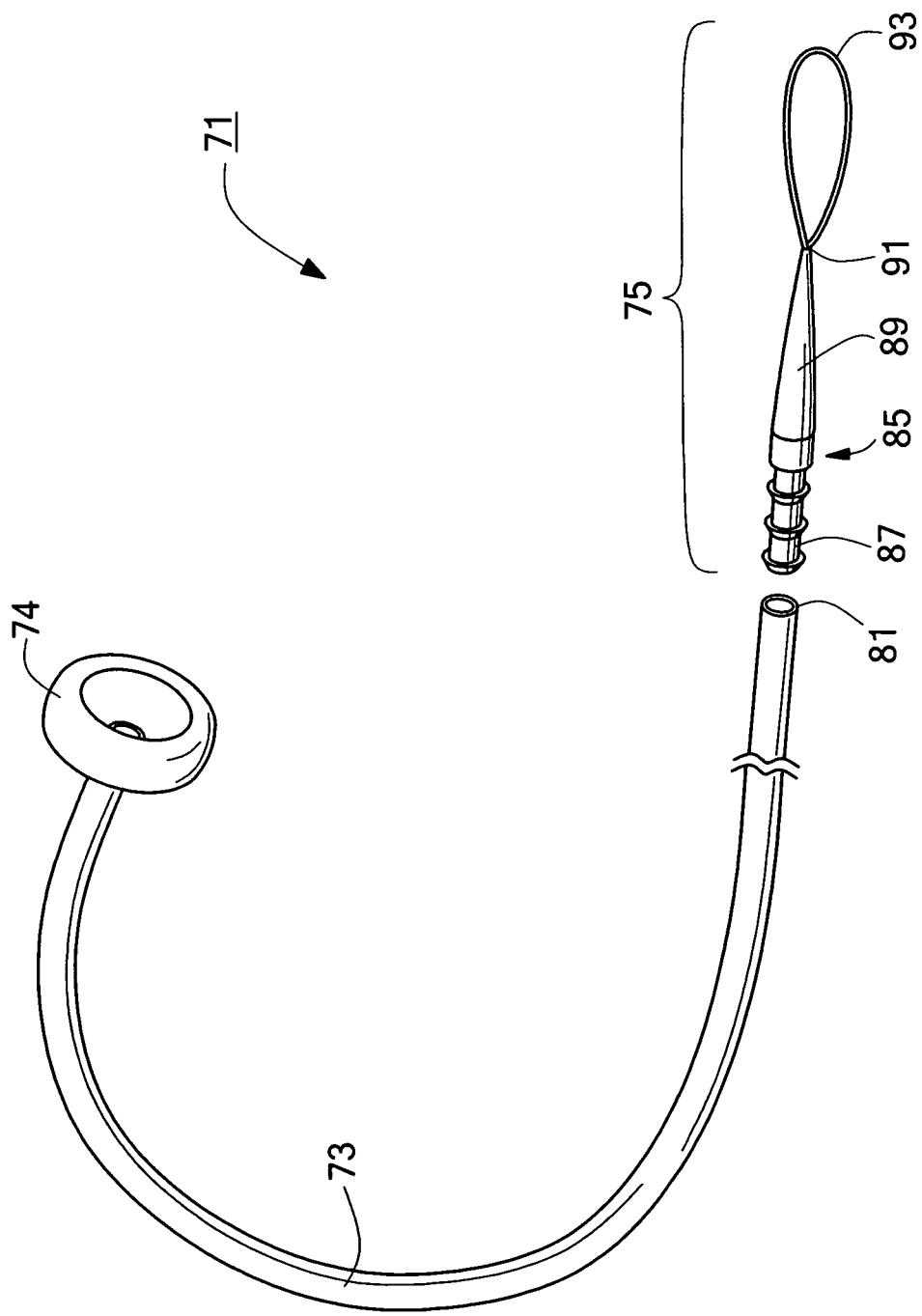
FIG. 3 is a fragmentary, partially exploded, perspective view of a conventional medical catheter assembly adapted for percutaneous endoscopic implantation in a patient using the pull method.

Referring now to FIG. 3, there is shown a fragmentary, partially exploded, perspective view of a conventional medical catheter assembly adapted for percutaneous endoscopic implantation in a patient using the pull method, said conventional medical catheter assembly being represented generally by reference numeral 71.

Assembly 71, which is shown prior to use on a patient, comprises a gastrostomy feeding tube 73, an internal bolster 74 and a fitting assembly 75.

Tube 73 and bolster 74 are indistinguishable in size, shape and composition from tube 13 and bolster 14, respectively, of assembly 11.

Fitting assembly 75 comprises a fitting 85. Fitting 85, which is made of a rigid plastic, is shaped to include a barbed rear portion 87 mounted within leading end 81 of tube 73 and a conical front portion 89 that serves as a dilator, front portion 89 tapering in diameter from a point proximate to leading end 81 of tube 73 to a front tip 91. A wire loop 93, which is adapted to be secured to the first end of a suture, is fixed (typically by insert-molding) to front tip 91.

Unfortunately, as noted above, assembly 71 often fails to withstand tensile forces in the range of about 17 pounds, with fitting 85 frequently being pulled out of tube 73.

Figure 4:
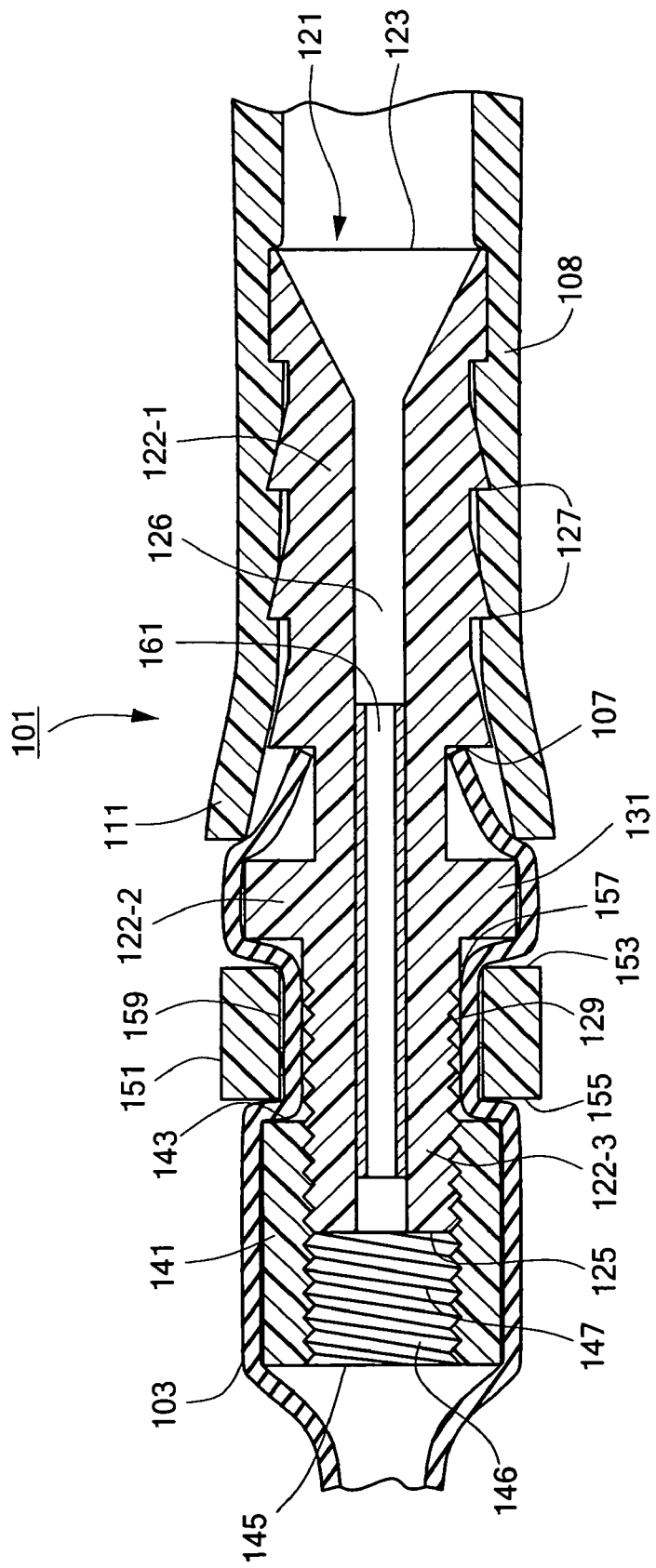
FIG. 4 is a fragmentary, longitudinal section view of a first embodiment of a medical catheter assembly constructed according to teachings of the present invention, said medical catheter assembly being adapted for percutaneous endoscopic use in a patient using the push method.
Figure 5:
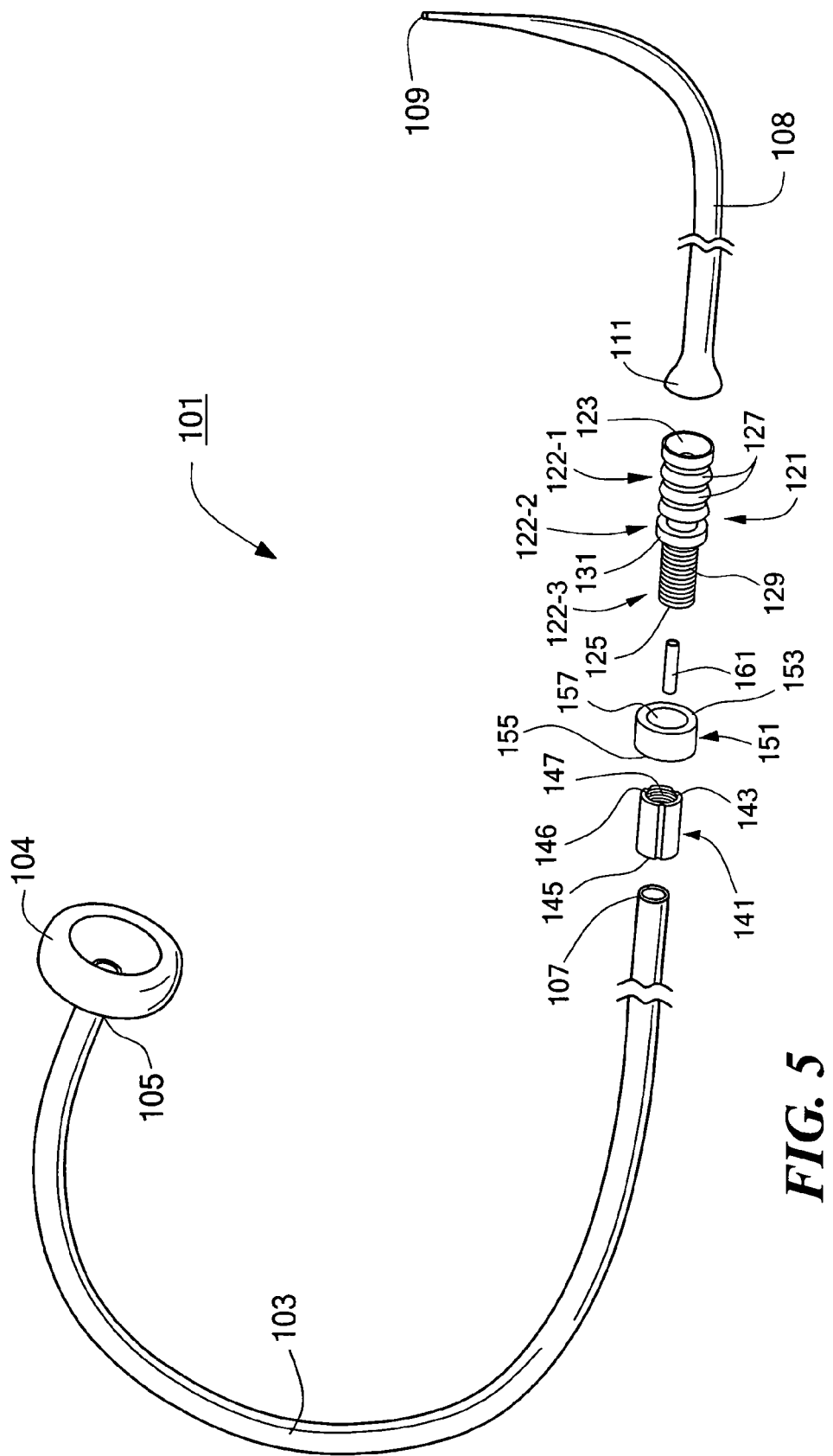
FIG. 5 is a fragmentary, exploded, perspective view of the medical catheter assembly of FIG. 4.

Referring now to FIGS. 4 and 5, there are shown fragmentary section and fragmentary exploded perspective views, respectively, of a first embodiment of a medical catheter assembly constructed according to teachings of the present invention and adapted for percutaneous endoscopic implantation in a patient using the push method, said medical catheter assembly being represented generally by reference numeral 101.

Assembly 101 comprises a gastrostomy feeding tube 103 and an internal bolster 104. Tube 103, which is similar to tube 13 of assembly 11, is an elongated, tubular member made of a soft, biocompatible, elastic material, such as a silicone rubber, and is shaped to include a trailing end 105 and a leading end 107. Although not wishing to be limited to any particular dimensions, tube 103 may have a length of about 2 feet and a diameter of 18 Fr., 20 Fr. or 24 Fr. A series of ruler markings (not shown) are printed on tube 103 and extend several inches from trailing end 105 in the direction of leading end 107 to facilitate the cutting of tube 103 to a desired length after it has been implanted in a patient.

Internal bolster 104, which is made of a soft, biocompatible, material, such as a silicone rubber, is securely disposed at trailing end 105 of tube 103 and, in the present embodiment, forms a unitary structure therewith.

Assembly 101 also comprises a dilator 108, dilator 108 being a unitary tubular member having a leading end 109 and a trailing end 111. Dilator 108 is made of a polyethylene having sufficient rigidity to open a stoma and, at the same time, sufficient flexibility to permit its being bent through a patient. Dilator 108 is dimensioned to gradually increase in diameter over a length of several inches from leading end 109, which is sized to conform closely to a guidewire inserted thereinto, to approximately the diameter of tube 103. Leading end 107 of tube 103 is inserted into dilator 108 through trailing end 111, trailing end 111 being outwardly flared, for example, by a flaring iron, to facilitate receiving leading end 107 of tube 103.

Figure 6A:
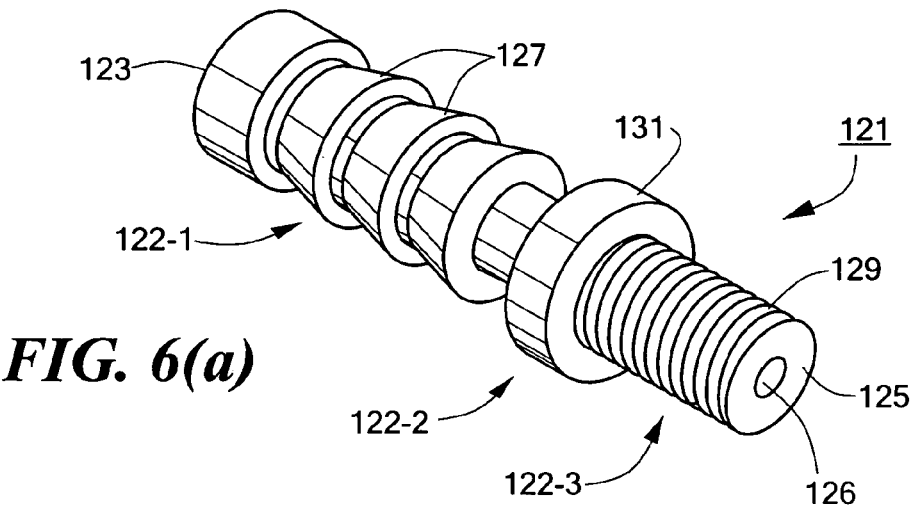
FIGS. 6(a) through 6(c) are enlarged perspective, section, and side views, respectively, of the fitting shown in FIG. 4.
Figure 6B:
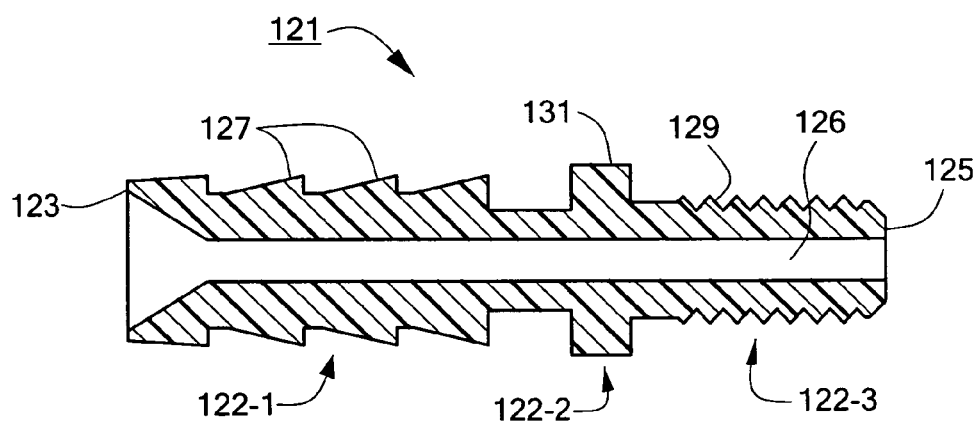
Figure 6C:
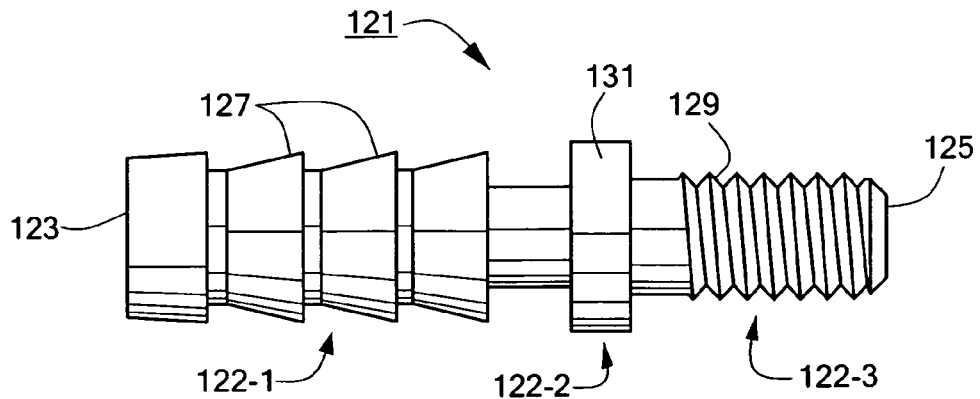

Assembly 101 additionally comprises a fitting 121 (shown separately in FIGS. 6(a) through 6(c)), fitting 121 being a unitary tubular member preferably made of a rigid material, such as a rigid molded plastic. Fitting 121 is shaped to include a front portion 122-1, an intermediate portion 122-2 and a rear portion 122-3, front portion 122-1 terminating in a leading end 123, rear portion 122-3 terminating in a trailing end 125. A longitudinal bore 126 extends the length of fitting 121, bore 126 being outwardly flared at its front end. Longitudinal bore 126 is appropriately sized to receive a guidewire therethrough. In this manner, assembly 101 may be advanced through a patient over said guidewire using the push method.

Leading end 123 of fitting 121 is coaxially inserted into dilator 108 through trailing end 111 and is secured within dilator 108 by a series of external barbs 127 formed on front portion 122-1. Trailing end 125 of fitting 121 is coaxially inserted into gastrostomy feeding tube 103 through leading end 107. An external helical thread 129, whose purpose will be discussed below, is integrally formed on rear portion 122-3 and extends from trailing end 125 to intermediate portion 122-2.

Intermediate portion 122-2 is shaped to include an external annular flange or shoulder 131, the purpose of shoulder 131 being discussed below.

Assembly 101 further comprises an inner ring 141 (shown separately in FIGS. 7(a) through 7(c)), inner ring 141 being a unitary tubular member preferably made of a rigid material, such as a rigid molded plastic, and having a leading end 143, a trailing end 145 and a longitudinal bore 146. Inner ring 141 is coaxially positioned within tube 103 at a certain depth, e.g., about 1.5 inches from leading end 107, and has an outer diameter that is greater than the inner diameter of tube 103; as a result, inner ring 141 is secured within tube 103 by a pressfit.

Longitudinal bore 146 of inner ring 141 is appropriately sized to receive trailing end 125 of fitting 121 therewithin, and an internal helical thread 147 is formed on the inner surface of inner ring 141 to matingly engage external helical thread 129 so as to lock together fitting 121 and ring 141.

Assembly 101 further comprises an outer ring 151 (shown separately in FIGS. 8(a) and 8(b)), outer ring 151 being a unitary tubular member preferably made of a rigid material, such as a rigid molded plastic, and having a leading end 153, a trailing end 155 and a longitudinal bore 157. Outer ring 151 coaxially surrounds tube 103 between shoulder 131 and inner ring 141 and has an inner diameter that is both slightly greater than trailing end 125 of fitting 121 and less than the outer diameters of shoulder 131 and inner ring 141, respectively. In this manner, with fitting 121 and ring 141 fully screwed together, tube 103 becomes securely coupled to fitting 121 through a pair of pinch points, one such pinch point being between leading end 153 of ring 151 and shoulder 131, the other such pinch point being between trailing end 155 of ring 151 and leading end 143 of ring 141. The outer diameter of outer ring 151 is preferably not much greater than the outer diameters of shoulder 131 and inner ring 141, respectively, so that the exterior of assembly 101 is substantially uniform over the region extending from that portion of tube 103 covering shoulder 131 to that portion of tube 103 covering inner ring 141.

Although the inner surface 159 of outer ring 151 is shown in the present embodiment as a straight surface, it can readily be appreciated that inner surface 159 could be chamfered at leading end 153 and/or trailing end 155 to facilitate the insertion of tube 103 through bore 157.

Assembly 101 preferably further comprises a hypotube 161, hypotube 161 being a unitary tubular member coaxially disposed within bore 126 towards the trailing end thereof to provide reinforcement to trailing end 125 of fitting 121 against damage caused by bending. Hypotube 161 is preferably made of stainless steel, and fitting 121 may be insert-molded around hypotube 161.

Assembly 101 has been tested by the present inventors, and the connection of dilator 108 to tube 103 therein has been found to meet the industry standard minimum tensile strength of 17 pounds.

To assemble assembly 101, inner ring 141 is inserted into tube 103 through leading end 107, preferably to a depth of about 1.5 inches. Next, leading end 107 of tube 103 is inserted through outer ring 151 until outer ring 151 is positioned just before inner ring 141. Next, rear portion 122-3 of fitting 121 is inserted through leading end 107 of tube 103 and into longitudinal bore 146 of inner ring 141. Fitting 121 and inner ring 141 are then screwed tightly together, causing tube 103 to be pinched between outer ring 151 and shoulder 131 and between outer ring 151 and inner ring 141. (If desired, a drop of medical grade glue may be placed at about the midsection of rear portion 122-2 prior to insertion of fitting 121 into tube 103 in order to strengthen the connection between fitting 121 and inner ring 141.) With fitting 121 and inner ring 141 thus screwed together, leading end 107 of tube 103 becomes tucked into the recessed area between shoulder 131 and barbs 127. Lastly, front portion 122-1 of fitting 121 is inserted into dilator 108 through trailing end 111, whereby barbs 127 of fitting 121 engage the inner surface of dilator 108 to retain fitting 121 therewithin. Once assembled, assembly 101 may be used in the same fashion as assembly 11.

As can readily be appreciated, the aforementioned assembly steps may be performed manually or may be automated to varying degrees.

In the present embodiment, each of fitting 121, inner ring 141 and outer ring 151 is preferably made of the same material, namely, a molded plastic, such as acetal. However, it can readily be appreciated that fitting 121, inner ring 141 and outer ring 151 need not be made of the same material and, in fact, need not even be made of molded plastic. For example, one or more of fitting 121, inner ring 141 and outer ring 151 could be made of stainless steel although the material costs and/or the fabrication costs (e.g., machining) would likely be greater for stainless steel than for molded plastic.

It should also be noted that, if one were to make fitting 121 and dilator 108 of the same material, such as polyethylene, one could omit barbs 127 from fitting 121 and then join fitting 121 to dilator 108 by spin-welding. (In such a case, the leading portion of fitting 121 would preferably have a conical or frustoconical shape to accommodate spin-welding.)

Similarly, provided that fitting 121 and inner ring 141 are made of the same material, fitting 121 and inner ring 141 may be joined together by spin-welding. (In such a case, threads 129 and 147 would preferably be omitted from fitting 121 and inner ring 141, respectively, and rear portion 122-3 of fitting 121 would preferably have a conical or frustoconical shape.)

It should also be noted that, although fitting 121 is disclosed in the present embodiment as a unitary structure, one could assemble fitting 121 from two or more separate pieces.

Referring now to FIG. 9, there is shown a fragmentary, section view of a second embodiment of a medical catheter assembly constructed according to teachings of the present invention, said medical catheter assembly being adapted for percutaneous endoscopic use in a patient using the push method and being represented generally by reference numeral 201.

Assembly 201 is similar in certain respects to assembly 101, the principal differences between the two assemblies being that assembly 201 does not include fitting 121 and inner ring 141, but instead, includes a fitting 203 and an inner ring 205, respectively. In addition, assembly 201 differs from assembly 101 in that assembly 201 does not include hypotube 161.

Fitting 203, which is shown separately in FIGS. 10(a) and 10(b), is similar in many respects to fitting 121, the principal difference between the two fittings being that fitting 203 includes a rear portion 207, instead of rear portion 122-3. Rear portion 207 comprises a pair of parallel legs 209-1 and 209-2, legs 209-1 and 209-2 having front ends 211-1 and 211-2, respectively, that are fixed to shoulder 131 and rear ends 213-1 and 213-2, respectively, that are adapted to be resiliently flexed towards one another. Rear ends 213-1 and 213-2 are shaped to include outwardly opposed feet 215-1 and 215-2, respectively, the purpose of which will become apparent below.

Figure 11A:
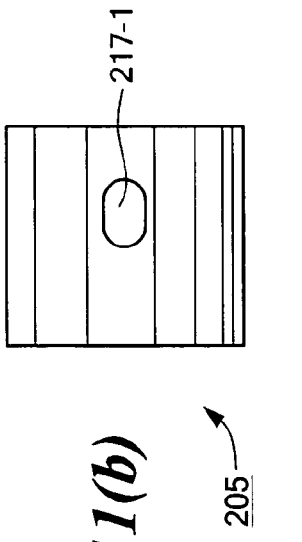
FIGS. 11(a) and 11(b) are perspective and side views, respectively, of the inner ring shown in FIG. 9.
Figure 11B:
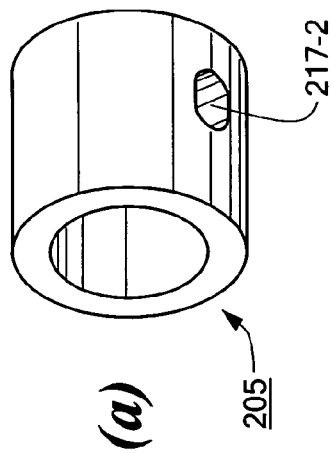

Inner ring 205, which is shown separately in FIGS. 11(a) and 11(b), is similar in many respects to inner ring 141, the principal difference between the two rings being that inner ring 205 does not include an internal helical thread 147, but rather, includes a pair of transverse openings 217-1 and 217-2, openings 217-1 and 217-2 being appropriately sized and positioned on ring 205 to receive feet 215-1 and 215-2, respectively.

Assembly 201 is assembled in much the same fashion as assembly 101, the principal difference between the two assemblies being that, with assembly 201, fitting 203 and inner ring 205 are coupled together by a snap-fit by inserting fitting 203 into inner ring 205 until that feet 215-1 and 215-2 are received in openings 217-1 and 217-2, respectively. Once assembled, assembly 201 is used in the same fashion as assembly 101.

Figure 12A:
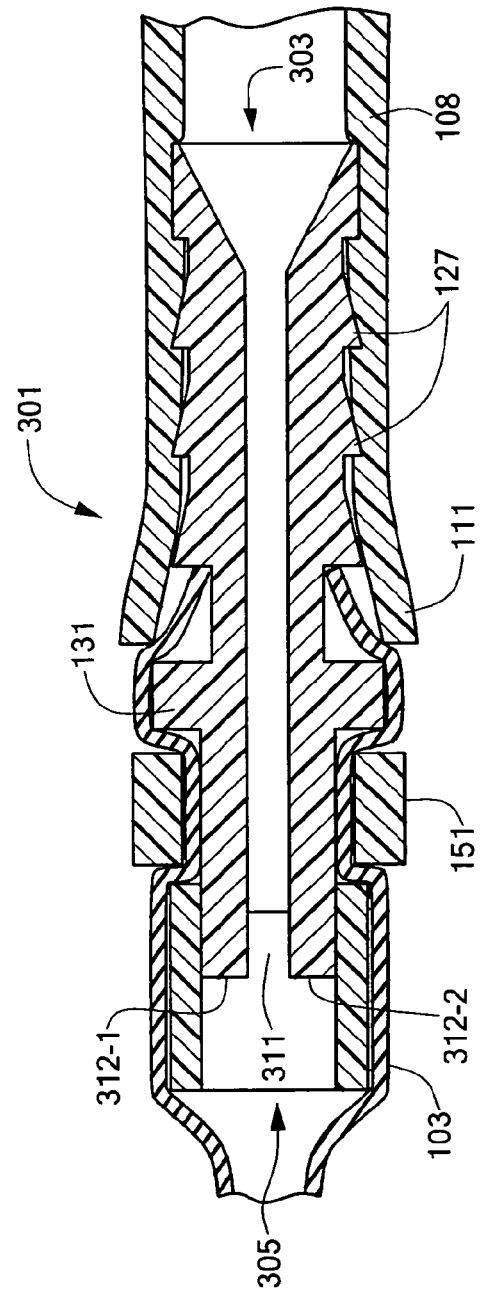
FIG. 12(a) is a fragmentary, longitudinal section view of a third embodiment of a medical catheter assembly constructed according to teachings of the present invention, said medical catheter assembly being adapted for percutaneous endoscopic use in a patient using the push method.

Referring now to FIGS. 12(a) and 12(b), there are shown fragmentary, longitudinal section and transverse section views, respectively, of a third embodiment of a medical catheter assembly constructed according to teachings of the present invention, said medical catheter assembly being adapted for percutaneous endoscopic use in a patient using the push method and being represented generally by reference numeral 301.

Assembly 301 is similar in certain respects to assembly 101, the principal differences between the two assemblies being that assembly 301 does not include fitting 121 and inner ring 141, but instead, includes a fitting 303 and an inner ring 305, respectively. In addition, assembly 301 differs from assembly 101 in that assembly 301 does not include hypotube 161.

Fitting 303, which is shown separately in FIGS. 13(a) and 13(b), is similar in many respects to fitting 121, the principal difference between the two fittings being that fitting 303 includes a rear portion 307, instead of rear portion 122-3. Rear portion 307 is generally tubular and is shaped to include a slot 311, slot 311 extending longitudinally forward a short distance from the rear end of rear portion 307 to define a pair of trailing end sections 312-1 and 312-2. A first L-shaped recess is provided in trailing end section 312-1, and a second L-shaped recess is provided in trailing end section 312-2. These L-shaped recesses, which are spaced 180 degrees apart along the circumference of rear portion 307, include circumferentially-extending portions 315-1 and 315-2, respectively, and longitudinally-extending portions 317-1 and 317-2, respectively. Each of circumferentially-extending portions 315-1 and 315-2 communicate at one end thereof with the forward end of slot 311, and each of longitudinally-extending portions 317-1 and 317-2 extend rearwardly a short distance.

Inner ring 305, which is shown separately in FIG. 14, is similar in many respects to inner ring 141, the principal difference between the two rings being that inner ring 305 does not include an internal helical thread 147, but rather, includes a pair of rectangular blocks 321-1 and 321-2 projecting radially inwardly a short distance from the inner surface of inner ring 305 at its leading end 323. Blocks 321-1 and 321-2 are appropriately sized and spaced apart on ring 305 so as to permit their insertion through slot 311 and into recesses 313-1 and 313-2, respectively.

Assembly 301 is assembled in much the same fashion as assembly 101, the principal difference between the two assemblies being that, with assembly 301, fitting 303 and inner ring 305 are coupled together through a U-lock by inserting fitting 303 into inner ring 305 until blocks 321-1 and 321-2 are advanced to the front end of slot 311, then twisting fitting 303 relative to inner ring 305 as far as possible to draw blocks 321-1 and 321-2 fully through circumferentially-extending portions 315-1 and 315-2, respectively, of recesses 313-1 and 313-2, respectively, and then pulling fitting 303 away from inner ring 305 as far as possible to draw blocks 321-1 and 321-2 fully through longitudinally-extending portions 317-1 and 317-2, respectively, of recesses 313-1 and 313-2. Once assembled, assembly 301 is used in the same fashion as assembly 101.

Figure 15:
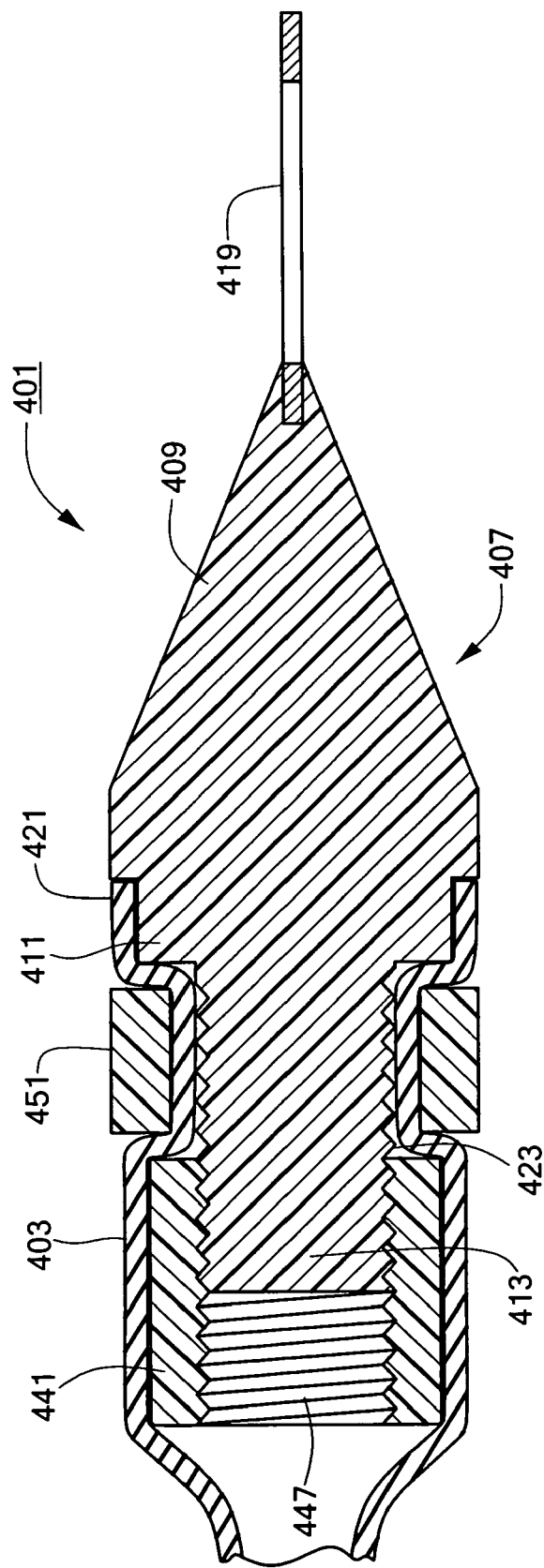
FIG. 15 is a fragmentary, longitudinal section view of a fourth embodiment of a medical catheter assembly constructed according to teachings of the present invention, said medical catheter assembly being adapted for percutaneous endoscopic use in a patient using the pull method.
Figure 16:
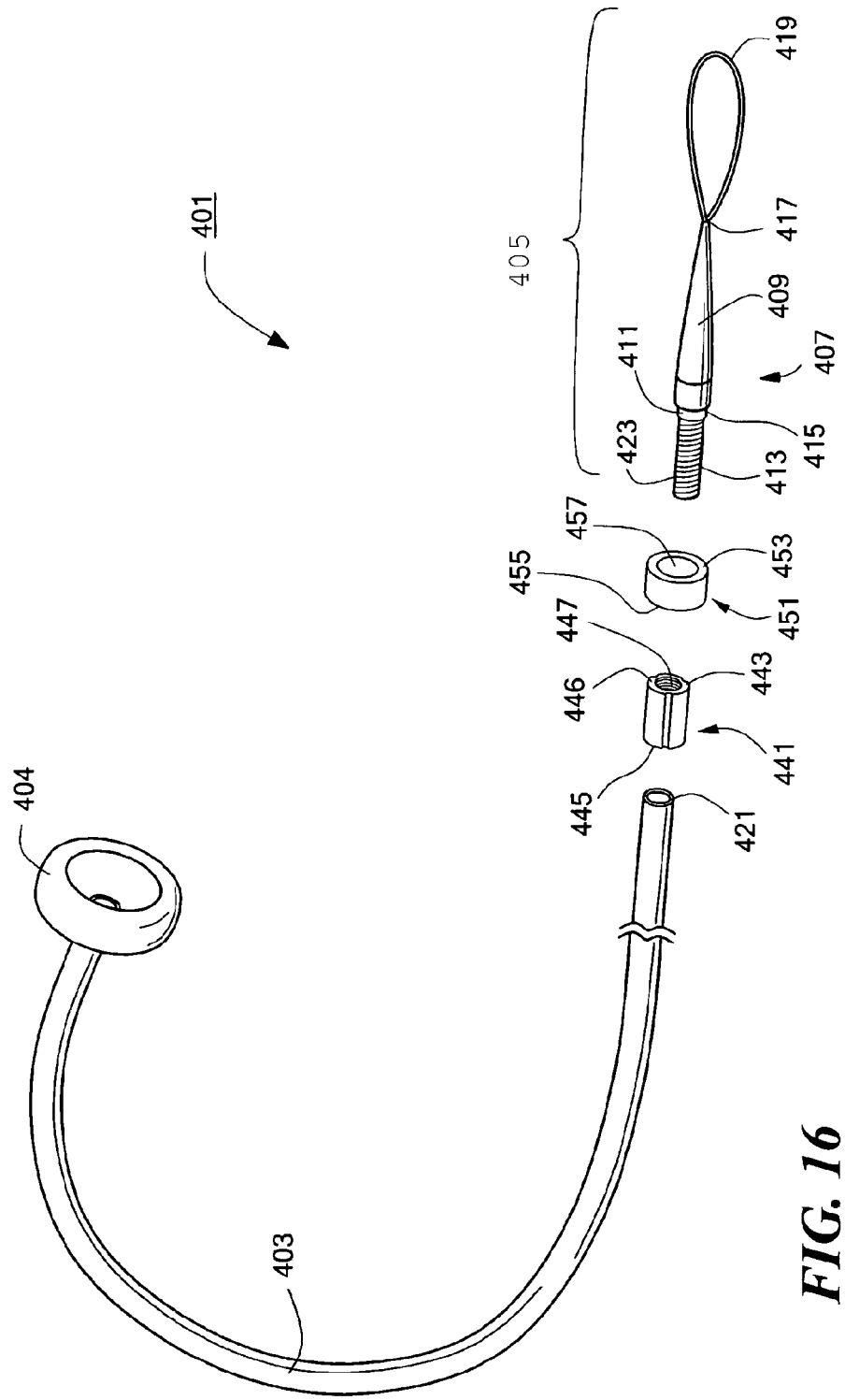
FIG. 16 is a partially exploded, perspective view of the medical catheter assembly shown in FIG. 15.

Referring now to FIGS. 15 and 16, there are shown fragmentary, section and partially-exploded, perspective views, respectively, of a fourth embodiment of a medical catheter assembly constructed according to teachings of the present invention, said medical catheter assembly being adapted for percutaneous endoscopic use in a patient using the pull method and being represented generally by reference numeral 401.

Assembly 401 comprises a gastrostomy feeding tube 403 and an internal bolster 404, tube 403 and bolster 404 being identical to tube 103 and bolster 104 of assembly 101.

Assembly 401 additionally comprises a fitting assembly 405, fitting assembly 405 comprising a fitting 407. Fitting 407, which is made of a rigid plastic, is shaped to include a front portion 409, an intermediate portion 411, and a rear portion 413. Front portion 409, which serves as a dilator, is conical in shape and tapers in diameter from its rear end 415 to a front tip 417. A wire loop 419, which is adapted to be secured to the first end of a suture, is fixed, preferably by insert-molding, to front tip 417.

Intermediate portion 411, which is cylindrical in shape and coaxial with front portion 409, is appropriately sized to snugly receive thereover the leading end 421 of tube 403 by a press-fit and, at the same time, hold leading end 421 of tube 403 so that it lies flush with rear end 415 of front portion 409.

Rear portion 413, which is cylindrical in shape and coaxial with intermediate portion 411, has a reduced diameter as compared to intermediate portion 411. An external helical thread 423, the purpose of which will become apparent below, is formed along the length of rear portion 413.

Assembly 401 further comprises an inner ring 441, inner ring 441 being similar to inner ring 141 of assembly 101. As such, inner ring 441 is a unitary tubular member preferably made of a rigid material, such as a rigid molded plastic, and has a leading end 443, a trailing end 445 and a longitudinal bore 446. Inner ring 441 is coaxially positioned within tube 403 at a certain depth, e.g., about 1.5 inches from leading end 421, and has an outer diameter that is greater than the inner diameter of tube 403; as a result, inner ring 441 is secured within tube 403 by a press-fit.

Longitudinal bore 446 of inner ring 441 is appropriately sized to receive rear portion 413 of fitting 407 therewithin, and an internal helical thread 447 is formed on the inner surface of inner ring 441 to matingly engage external helical thread 423 so as to lock together fitting 407 and ring 441.

Assembly 401 further comprises an outer ring 451, outer ring 451 being similar to outer ring 151 of assembly 101. As such, outer ring 451 is a unitary tubular member preferably made of a rigid material, such as a rigid molded plastic, and has a leading end 453, a trailing end 455 and a longitudinal bore 457. Outer ring 451 coaxially surrounds tube 403 between intermediate portion 411 of fitting 407 and inner ring 441 and has an inner diameter that is both slightly greater than rear portion 413 of fitting 407 and less than the outer diameters of intermediate portion 411 and inner ring 441, respectively. In this manner, with fitting 407 and ring 441 fully screwed together, tube 403 becomes securely coupled to fitting 407 through a pair of pinch points, one such pinch point being between leading end 453 of ring 451 and the rear end of intermediate portion 411 (the rear end of intermediate portion 411 functioning analogously to shoulder 131 of assembly 101), the other such pinch point being between trailing end 455 of ring 451 and leading end 443 of ring 441. The outer diameter of outer ring 451 is preferably not much greater than the outer diameters of intermediate portion 411 and inner ring 441, respectively, so that the exterior of assembly 401 is substantially uniform in diameter over the region extending from that portion of tube 403 covering intermediate portion 411 to that portion of tube 403 covering inner ring 441.

To assemble assembly 401, inner ring 441 is inserted into tube 403 through leading end 421, preferably to a depth of about 1.5 inches. Next, leading end 421 of tube 403 is inserted through outer ring 451 until outer ring 451 is positioned just before inner ring 441. Next, rear portion 413 of fitting 407 is inserted through leading end 421 of tube 403 and into longitudinal bore 446 of inner ring 441. Fitting 407 and inner ring 441 are then screwed tightly together, causing leading end 421 of tube 403 to be drawn over intermediate portion 411 and causing tube 403 to be pinched between outer ring 451 and intermediate portion 411 and between outer ring 451 and inner ring 441. (If desired, a drop of medical grade glue may be placed at about the midsection of rear portion 413 prior to insertion of fitting 407 into tube 403 in order to strengthen the connection between fitting 407 and inner ring 441.) Once assembled, assembly 401 may be used in the same fashion as assembly 71.

It should be noted that, although the assemblies of the present invention have been described in the context of implanting tubes as part of percutaneous endoscopic gastrostomies, the present assemblies could also be used to implant catheters as part of any number of other medical procedures including, but not limited to, percutaneous endoscopic jejunostomies. Moreover, the connectors used in the push-type medical catheter assemblies described herein are not limited to use in catheter implanting assemblies and may be used to join together various types of tubing for a wide variety of different applications.

The embodiments of the present invention described above are intended to be merely exemplary and those skilled in the art shall be able to make numerous variations and modifications to it without departing from the spirit of the present invention. For example, although specific mechanical arrangements are disclosed herein for coupling together the fitting and inner ring components of the connector, other arrangements could easily be devised. All such variations and modifications are intended to be within the scope of the present invention as defined in the appended claims.

What is claimed is:

1. A medical catheter assembly comprising:
    (a) a medical catheter;
    (b) a first tubular member, said first tubular member being secured within said medical catheter;
    (c) a fitting, said fitting comprising a shoulder and a rear portion, said rear portion being positioned within said first tubular member and secured thereto, said shoulder being positioned in front of said rear portion; and
    (d) a second tubular member, said second tubular member being inserted over said medical catheter and positioned between said shoulder and said first tubular member, said second tubular member being appropriately sized to securely retain said medical catheter between said second tubular member and said first tubular member and to securely retain said medical catheter between said second tubular member and said shoulder.

2. The medical catheter assembly as claimed in claim 1 wherein said medical catheter surrounds said shoulder.

3. A medical catheter assembly comprising:
    (a) a medical catheter, said medical catheter being made of an elastic material and having a front end, a rear end and an inner diameter;
    (b) a first tubular member, said first tubular member having an outer diameter greater than the inner diameter of said medical catheter, said first tubular member being coaxially disposed within said medical catheter and secured thereto by a friction-fit;
    (c) a fitting, said fitting comprising a shoulder and a rear portion, said shoulder being positioned in front of said rear portion and having an outer diameter greater than the inner diameter of said medical catheter, said shoulder and said rear portion being inserted into said medical catheter through said front end, with said rear portion inserted into said first tubular member and secured thereto; and
    (d) a second tubular member, said second tubular member being inserted over said medical catheter and positioned between said shoulder and said first tubular member, said second tubular member being appropriately sized to securely retain said medical catheter between said second tubular member and said first tubular member and to securely retain said medical catheter between said second tubular member and said shoulder.

4. The medical catheter assembly as claimed in claim 3 wherein said first tubular member is provided with an internal thread, wherein said rear portion of said fitting is provided with an external thread and wherein said first tubular member and said rear portion of said fitting are secured to one another by threaded engagement of said internal thread and said external thread.

5. The medical catheter assembly as claimed in claim 3 wherein said first tubular member is provided with a transverse opening, wherein said rear portion of said fitting is provided with a resilient leg, said resilient leg having a foot adapted for insertion through said transverse opening and wherein said first tubular member and said rear portion of said fitting are secured to one another by insertion of said foot through said transverse opening.

6. The medical catheter assembly as claimed in claim 3 wherein said first tubular member is provided with a pair of transverse openings, wherein said rear portion of said fitting is provided with a pair of resilient legs, each of said resilient legs having a foot adapted for insertion through one of said transverse openings and wherein said first tubular member and said rear portion of said fitting are secured to one another by insertion of said feet through said transverse openings.

7. The medical catheter assembly as claimed in claim 3 wherein said first tubular member is provided with a projection extending radially inwardly, wherein said rear portion of said fitting is provided with a recess adapted to receive said projection and wherein said first tubular member and said rear portion of said fitting are secured to one another by insertion of said projection into said recess.

8. The medical catheter assembly as claimed in claim 3 wherein said first tubular member is provided with a pair of opposing projections extending radially inwardly, wherein said rear portion of said fitting is provided with a slot and a pair of L-shaped recesses, said slot extending longitudinally from a rear end of said rear portion of said fitting and adapted for insertion of said pair of opposing projections therethrough, one of said L-shaped recesses being adapted to receive one of said pair of opposing projections, the other of said L-shaped recesses being adapted to receive the other of said pair of opposing projections, each of said L-shaped recesses having a circumferentially-extending section communicating with said slot and a longitudinally-extending section extending towards said first end, and wherein said first tubular member and said rear portion of said fitting are secured to one another by inserting said projections through said slot, through said circumferentially-extending sections of said L-shaped recesses and into said longitudinally-extending sections of said L-shaped recesses.

9. The medical catheter assembly as claimed in claim 3 wherein said first tubular member and said rear portion of said fitting are secured to one another by spin-welding.

10. The medical catheter assembly as claimed in claim 3 wherein said medical catheter is a silicone tube.

11. The medical catheter assembly as claimed in claim 3 wherein said fitting further has a front portion in front of said shoulder, said front portion extending beyond said front end of said medical catheter, said front portion of said fitting being conical in shape and coming to a tip at a front end of said fitting.

12. The medical catheter assembly as claimed in claim 11 further comprising a wire loop, said wire loop extending forwardly from said front end of said fitting.

13. The medical catheter assembly as claimed in claim 3 wherein said fitting further has a front portion in front of said shoulder, said front portion of said fitting extending beyond said medical catheter and shaped to include at least one barb.

14. The medical catheter assembly as claimed in claim 13 wherein said front portion of said fitting is shaped to include a plurality of barbs.

15. The medical catheter assembly as claimed in claim 13 wherein said fitting is provided with a longitudinal bore.

16. The medical catheter assembly as claimed in claim 3 wherein said fitting further comprises a closed front portion in front of said shoulder, said medical catheter assembly further comprising a length of tubing, said length of tubing comprising a front end and a rear end, said front portion of said fitting being inserted into said length of tubing through said rear end thereof and secured within said length of tubing.

17. The medical catheter assembly as claimed in claim 16 wherein said front portion of said fitting is shaped to include at least one barb for securing said front portion of said fitting within said length of tubing.

18. The medical catheter assembly as claimed in claim 16 wherein said medical catheter is a feeding tube and wherein said length of tubing is a dilator.

19. The medical catheter assembly as claimed in claim 18 wherein said dilator has an outwardly flared rear end.

20. The medical catheter assembly as claimed in claim 18 further comprising an internal bolster, said internal bolster being disposed at said rear end of said feeding tube.

21. A medical catheter assembly comprising:
(a) a medical catheter, said medical catheter being made of an elastic material and having a front end, a rear end and an inner diameter;
(b) a first tubular member, said first tubular member having an outer diameter greater than an inner diameter of said medical catheter, said first tubular member being coaxially disposed within said medical catheter and secured thereto by a friction-fit;
(c) a fitting, said fitting comprising a front portion, a shoulder and a rear portion, said shoulder being positioned between said front portion and said rear portion and having an outer diameter greater than the inner diameter of said medical catheter, said shoulder and said rear portion being inserted into said medical catheter through a front end of said medical catheter, with said rear portion inserted into said first tubular member and secured thereto;
(d) a second tubular member, said second tubular member being inserted over said medical catheter and positioned between said shoulder and said first tubular member, said second tubular member being appropriately sized to securely retain said medical catheter between said second tubular member and said first tubular member and to securely retain said medical catheter between said second tubular member and said shoulder; and
(e) a length of tubing, said length of tubing having a front end and a rear end, said front end of said fitting being inserted into said length of tubing through said rear end thereof and secured within said length of tubing.

22. The medical catheter assembly as claimed in claim 21 wherein said front portion of said fitting is shaped to include at least one barb for securing said front portion of said fitting within said length of tubing.

23. The medical catheter assembly as claimed in claim 21 wherein said medical catheter is a feeding tube and wherein said length of tubing is a dilator.

24. The medical catheter assembly as claimed in claim 23 further comprising an internal bolster, said internal bolster being disposed at said rear end of said feeding tube.

25. The medical catheter assembly as claimed in claim 21 wherein said fitting further comprises a longitudinal bore.

26. A connector for connecting a first length of tubing to a second length of tubing, the first length of tubing being made of an elastic material, said connector comprising:
(a) a first tubular member, said first tubular member having an outer diameter greater than the inner diameter of said first length of tubing, said first tubular member being adapted to be coaxially inserted into said first length of tubing and secured therewithin by a friction-fit;
(b) a fitting, said fitting comprising a front portion, a shoulder and a rear portion, said shoulder being positioned between said front portion and said rear portion and having an outer diameter greater than the inner diameter of said first length of tubing, said shoulder and said rear portion being adapted to be coaxially inserted into said first length of tubing, said rear portion of said fitting being adapted to be coaxially inserted into said first tubular member and secured thereto, said front portion of said fitting being adapted to be coaxially inserted into said second length of tubing and secured thereto; and
(c) a second tubular member, said second tubular member being adapted to be inserted over said first length of tubing and positioned between said shoulder and said first tubular member, said second tubular member being appropriately sized so that, with said fitting and said first tubular member secured to one another, said first length of tubing may be securely retained between said second tubular member and said first tubular member and between said second tubular member and said shoulder.

27. A connector for use with a first length of tubing, the first length of tubing being made of an elastic material, said connector comprising:
(a) a first tubular member, said first tubular member having an outer diameter greater than the inner diameter of said first length of tubing, said first tubular member being adapted to be coaxially inserted into said first length of tubing and secured therewithin by a friction-fit;
(b) a fitting, said fitting comprising a front portion, a shoulder and a rear portion, said shoulder being positioned between said front portion and said rear portion and having an outer diameter greater than the inner diameter of said first length of tubing, said shoulder and said rear portion being adapted to be coaxially inserted into said first length of tubing, with said rear portion of said fitting being adapted to be coaxially inserted into said first tubular member and secured thereto, said front portion of said fitting being conical in shape and terminating in a tip at a front end thereof;
(c) a wire loop extending forwardly from said front end of said fitting; and
(d) a second tubular member, said second tubular member being adapted to be inserted over said first length of tubing and positioned between said shoulder and said first tubular member, said second tubular member being appropriately sized so that, with said fitting and said first tubular member secured to one another, said first length of tubing may be securely retained between said second tubular member and said first tubular member and between said second tubular member and said shoulder.

28. The medical catheter assembly as claimed in claim 1 wherein said second tubular member forms a first pinch point in the medical catheter between said second tubular member and said first tubular member, and forms a second pinch point in the medical catheter between said second tubular member and said shoulder.

* * * * *